United States Patent
Xu et al.

(10) Patent No.: US 11,963,997 B2
(45) Date of Patent: Apr. 23, 2024

(54) ANTI-TUMOR POLYPEPTIDE BAX-BH3, FLUORESCENT POLYMERIC NANOMICELLE, PREPARATION METHOD AND USE THEREOF

(71) Applicant: Jilin University, Changchun (CN)

(72) Inventors: Li Xu, Changchun (CN); Yi Guo, Changchun (CN); Sijun Huang, Changchun (CN); Xi Zhang, Changchun (CN); Mingming Zhang, Changchun (CN)

(73) Assignee: Jilin University (CN)

( * ) Notice: Subject to any disclaimer, the term of this patent is extended or adjusted under 35 U.S.C. 154(b) by 0 days.

(21) Appl. No.: 17/812,934

(22) Filed: Jul. 15, 2022

(65) Prior Publication Data
US 2023/0037813 A1  Feb. 9, 2023

(30) Foreign Application Priority Data
Jul. 21, 2021  (CN) .......................... 202110823372.4

(51) Int. Cl.
 A61K 47/34  (2017.01)
 A61K 38/17  (2006.01)
 A61K 47/32  (2006.01)
 A61K 49/00  (2006.01)
 A61P 35/00  (2006.01)

(52) U.S. Cl.
 CPC .......... *A61K 38/1709* (2013.01); *A61K 47/32* (2013.01); *A61K 49/0082* (2013.01); *A61P 35/00* (2018.01)

(58) Field of Classification Search
None
See application file for complete search history.

(56) References Cited

U.S. PATENT DOCUMENTS

2003/0139344 A1  7/2003  Hung et al.

FOREIGN PATENT DOCUMENTS

| CN | 101302256 A | 11/2008 |
|---|---|---|
| CN | 102958940 A | 3/2013 |
| CN | 106565835 A | 4/2017 |
| CN | 107111691 B | 1/2021 |
| CN | 112843247 A | 5/2021 |
| WO | 0059526 A1 | 10/2000 |

OTHER PUBLICATIONS

Utama, Robert H. et al; "Synthesis of hollow polymeric nanoparticles for protein delivery via inverse miniemulsion periphery raft polymerization." Chem. Comm. (2012) 48 p. 11103-11105.*
Billen, L. P. et al., "Bid: a Bax-like BH3 protein", Oncogene 27(Suppl 1):S93-104 (2008). (Abstract only).
Bohler, Sheila et al., "Inhibition of the anti-apoptotic protein MCL-1 severely suppresses human hematopoiesis", Haematologica 106(12):3136-3148 (2021).
Cory, Suzanne et al., "Targeting BXL-2-like Proteins to Kill Cancer Cells", Trends in Cancer 2(8):443-460 (2016).
George, Nicholas et al., "A three-helix homo-oligomerization domain containing BH3 and BH1 is responsible for the apoptotic activity of Bax", Genes & Development 21:1937-1948 (2007).
Juin, Philippe et al. "Activation of Bax by BH3 Domains during Apoptosis: The zunfolding of a Deadly Plot", Cell Cycle 4(5):637-642 (2005).
Peng, Jun et al., "The Bax BH3 Peptide H2-H3 Promotes Apoptosis by Inhibiting Bcl-2's Pore-Forming and Anti-Bax Activities in the Membrane", Sheng Wu Yi Xue Gong Cheng Xue Za Zhi 26(4):829-835 (2009).
Vieira, Helena L.A. et al., "Cell permeable BH3-peptides overcome the cytoprotective effect of Bcl-2 and Bcl-XL", Oncogene 21:1963-1977 (2002).
Zhang, Jing and Yang, Qing "The study of BH3 domain proteins (BOPs) and Bax only", Medical Review 23:1417-1419 (2006). (Abstract only).

* cited by examiner

*Primary Examiner* — Fred H Reynolds
(74) *Attorney, Agent, or Firm* — Lerner David LLP

(57) ABSTRACT

The present disclosure provides an anti-tumor polypeptide Bax-BH3, a fluorescent polymeric nanomicelle, a preparation method and use thereof, belonging to the technical field of medicines. The anti-tumor polypeptide Bax-BH3 has an amino acid sequence set forth in SEQ ID No: 1; the fluorescent polymeric nanomicelle includes the anti-tumor polypeptide Bax-BH3 and a polymer carrier; and the polymer carrier is a block copolymer RGD-PHPMA-b-Poly (MMA-alt-(Rhob-MA)). In the present disclosure, the anti-tumor polypeptide Bax-BH3 has desirable biocompatibility and biological activity; and the fluorescent polymeric nanomicelle encapsulates the anti-tumor polypeptide Bax-BH3 by the block copolymer RGD-PHPMA-b-Poly(MMA-alt-(Rhob-MA)), with high encapsulation rate and drug loading, and good release performance.

7 Claims, 15 Drawing Sheets

Specification includes a Sequence Listing.

a:PHPMA-b-Poly(MMA-alt-(Rhob-MA))
b:PHPMA-b-Poly(MMA-alt-(Rhob-MA))@BH$_3$
a:-RGD-PHPMA-b-Poly(MMA-alt-(Rhob-MA))@BH$_3$

SEQUENCE LISTING

```
Sequence total quantity: 4
SEQ ID NO: 1            moltype = AA   length = 20
FEATURE                 Location/Qualifiers
source                  1..20
                        mol_type = protein
                        note = amino acid sequence of anti-tumor polypeptide Bax-BH3
                        organism = synthetic construct
SEQUENCE: 1
DASTKKLSEC LRRIGDELDS                                                  20

SEQ ID NO: 2            moltype = DNA   length = 63
FEATURE                 Location/Qualifiers
source                  1..63
                        mol_type = other DNA
                        note = nucleotide sequence encoding anti-tumor polypeptide
                         Bax-BH3
                        organism = synthetic construct
```

```
SEQUENCE: 2
atggatgcgt ccaccaagaa gctgagcgag tgtctccggc gaattggaga tgaactggac    60
agc                                                                 63

SEQ ID NO: 3           moltype = DNA   length = 30
FEATURE                Location/Qualifiers
source                 1..30
                       PCR_primers =
                         fwd_name:upstream_primer,fwd_seq:ccgctcgagatggatgcgtccaccaa
                         gaag,rev_name:downstream_primer,rev_seq:ccggaattcgctgtccagt
                         tcatctcc
                       mol_type = other DNA
                       note = upstream primer sequence
                       organism = synthetic construct
SEQUENCE: 3
ccgctcgaga tggatgcgtc caccaagaag                                    30

SEQ ID NO: 4           moltype = DNA   length = 27
FEATURE                Location/Qualifiers
source                 1..27
                       PCR_primers =
                         fwd_name:upstream_primer,fwd_seq:ccgctcgagatggatgcgtccaccaa
                         gaag,rev_name:downstream_primer,rev_seq:ccggaattcgctgtccagt
                         tcatctcc
                       mol_type = other DNA
                       note = downstream primer sequence
                       organism = synthetic construct
SEQUENCE: 4
ccggaattcg ctgtccagtt catctcc                                       27
```

ANTI-TUMOR POLYPEPTIDE BAX-BH3, FLUORESCENT POLYMERIC NANOMICELLE, PREPARATION METHOD AND USE THEREOF

CROSS REFERENCE TO RELATED APPLICATION

This patent application claims the benefit and priority of Chinese Patent Application No. 202110823372.4, entitled "Anti-tumor polypeptide Bax-BH3, fluorescent polymeric nanomicelle, preparation method and use thereof" filed on Jul. 21, 2021, the disclosure of which is incorporated by reference herein in its entirety as part of the present application.

REFERENCE TO AN ELECTRONIC SEQUENCE LISTING

The contents of the electronic sequence listing (20220711_01980_UTL_Seq.xml; Size: 5,846 bytes; and Date of Creation: Jul. 4, 2022) is herein incorporated by reference in its entirety.

TECHNICAL FIELD

The present disclosure belongs to the technical field of medicines, in particular relates to an anti-tumor polypeptide Bax-BH3, a fluorescent polymeric nanomicelle, a preparation method and use thereof.

BACKGROUND ART

Apoptosis refers to the autonomous and orderly death of cells controlled by genes in order to maintain the stability of internal environment. Different from cell necrosis, apoptosis is not a passive process, but an active process, which involves the activation, expression and regulation of a series of genes. Apoptosis is not a phenomenon of autologous injury under pathological conditions, but a death process actively striving for better adaptation to the living environment. Apoptosis is critical for the development of multicellular animals, and dysregulation of normal apoptosis generally leads to various diseases, such as cancer, neurodegenerative diseases, and autoimmune diseases. Tumor cells can be immortalized by modifying normal apoptosis.

There are many biomolecules involved in regulating apoptosis, such as Bcl-2 family proteins. The family includes many members, such as Mcl-1, NR-B, A1, Bcl-w, Bcl-x, Bax, Bak, Bad, and Bim, which have both anti-apoptotic and pro-apoptotic effects separately. Most members have two regions of structural homology, playing an important role in mediating dimerization between the members. Dimerization among the Bcl-2 family protein members is an important form of functional realization or regulation among the members.

Bcl-2 associated X protein (Bax protein), as a pro-apoptotic protein in the Bcl-2 family, is related to apoptosis. The Bax protein generally exists in the cytoplasm. Once receiving a death message, Bax will be activated and transferred to the outer mitochondrial membrane; and oligomerization of the Bax protein changes permeability of the outer mitochondrial membrane to release Cyt c in mitochondria, thereby including apoptosis. (Suzanne, Cory, Andrew, el al. Targeting BCL-2-like Proteins to Kill Cancer Cells [J]. *Trends in Cancer,* 2016, 2(8): 443.).

All members of Bcl-2 family proteins include 1 to 4 Bcl-2 homology domains, where BH4 is a domain specific to anti-apoptotic proteins, and BH3 is a domain related to the promotion of apoptosis. In vitro experiments show that Bik, which is expressed in large quantities as the BH3 domain, can induce apoptosis alone, and introduction of the BH3 domain derived from Bax proteins into cells can also induce apoptosis. (Nicholas M. George, Jacquelynn J. D. Evans, and Xu Luo. A three-helix homo-oligomerization domain containing BH3 and BH1 is responsible for the apoptotic activity of Bax [J]. *Genes & Development,* 2007, 21(15): 1937-1948.).

Tumor cells restrict Bax activation by forming a Bcl-2/Bax dimer through overexpressing the Bcl-2 family proteins, or prevent the Bax activation by forming a dimer with Bak through overexpressing Mcl-1 and/or Bcl-xL proteins, such that apoptosis cannot be initiated. Accordingly, the tumor cells can escape apoptosis to achieve immortality. BH3-only proteins are the hubs that regulate the interactions between Bcl-2 family proteins. The BH3-only proteins can compete for binding to Bcl-2-like proteins to release Bax and Bak from Bcl-2/Mcl-1, or directly activate Bax/Bak, thereby promoting apoptosis.

BH3 domain is a consensus domain among the Bcl-2 family protein members and mediates interactions between the member proteins. The BH3 domain can induce apoptosis by competitively binding to one or more pro-apoptotic proteins to release Bax/Bak or directly activating the Bax/Bak. In contrast, traditional anticancer drugs generally need to activate upstream signaling pathways such as p53 (Vieira H L, Boya P, Cohen I, et al. Cell permeable BH3-peptides overcome the cytoprotective effect of Bcl-2 and Bcl-X [J]. *Oncogene,* 2008, 27, 6207-6215.); however, mutations or deletions of p53 occur in more than half of clinical tumor patients, resulting in resistance to conventional chemotherapy or radiotherapy. However, BH3 peptides can bypass the activation and directly competitively bind to Bcl-2 pro-apoptotic protein to release Bax/Bak, or directly activate the Bax/Bak, thereby activating tumor cell apoptosis program to induce tumor cell apoptosis. Therefore, the BH3 peptides can be used clinically in tumor patients resistant to chemotherapeutic drugs. However, further use of Bax-BH3 peptides in the field of cancer therapy is limited due to the fact that the chemical nature of Bax-BH3 peptide is polypeptides, which has the problems of short circulation time in vivo, easy degradation, and difficulty in effective intake by tumor cells.

SUMMARY

In view of this, an objective of the present disclosure is to provide an anti-tumor polypeptide Bax-BH3, a fluorescent polymeric nanomicelle, a preparation method and use thereof. The anti-tumor polypeptide Bax-BH3 has desirable biocompatibility and biological activity; and the fluorescent polymeric nanomicelle encapsulates the anti-tumor polypeptide Bax-BH3 by the block copolymer RGD-PHPMA-b-Poly(MMA-alt-(Rhob-MA)), with high encapsulation efficiency and drug loading, and excellent release performance.

To achieve the above objective, the present disclosure provides the following technical solutions.

The present disclosure provides an anti-tumor polypeptide Bax-BH3, having an amino acid sequence set forth in SEQ ID No: 1.

The present disclosure further provides an anti-tumor drug, including the anti-tumor polypeptide Bax-BH3 and auxiliary materials.

The present disclosure further provides a polymer carrier, wherein the polymer carrier is a block copolymer, named arginyl glycyl aspartic acid-poly(N-(2-hydroxypropyl)methacrylamide)-block polymethacryloyl rhodamine B-polymethyl methacrylate, abbreviated as RGD-PHPMA-b-Poly (MMA-alt-(Rhob-MA)).

The present disclosure further provides a method for preparing the polymer carrier, including the following steps:
1) reducing rhodamine B to synthesize reduced rhodamine B, and functional modifying the reduced rhodamine B with methacryloyl chloride to obtain methacryloyl-functionalized rhodamine B (Rhob-MA);
2) subjecting methyl methacrylate (MMA), 4-cyanopentanoic acid dithiobenzoate (CPADB), azobisisobutyronitrile (AIBN), and Rhob-MA to a reaction under $N_2$ protection and using tetrahydrofuran (THF) as a reaction solvent at 70° C. for 6 h after three times of freeze-thawing and degassing to obtain a product I, precipitating the product I with petroleum ether to obtain a precipitate 1, and vacuum-drying the precipitate 1 to obtain a purified product polymethacryloyl rhodamine B-polymethyl methacrylate, abbreviated as Poly(MMA-alt-(Rhob-MA));
3) subjecting hydroxypropyl methacrylate (HPMA), AIBN, and the Poly(MMA-alt-(Rhob-MA)) to a reaction under $N_2$ protection and by using THF as a reaction solvent at 70° C. for 12 h after three times of freeze-thawing and degassing to obtain a product II, precipitating the product II with diethyl ether to obtain a precipitate II, and vacuum-drying the precipitate II to obtain a purified product PHPMA-b-Poly(MMA-alt-(Rhob-MA));
4) subjecting N-hydroxy succinimide (NHS), 1-ethyl-3-(−3-dimethylaminopropyl) carbodiimide hydrochloride (EDC), and the PHPMA-b-Poly(MMA-alt-(Rhob-MA)) to a reaction with a 2-(N-morpholino)ethanesulfonic acid (MES) buffer as a reaction solvent at 20° C. to 25° C. for 24 h to obtain a product III; drying the product III and filtering with THF, and collecting a filtrate to obtain a purified product NHS-PHPMA-b-Poly(MMA-alt-(Rhob-MA)); and
5) subjecting the NHS-PHPMA-b-Poly(MMA-alt-(Rhob-MA)) and arginyl glycyl aspartic acid (RGDfK) to a reaction with an MES buffer as a reaction solvent at 20° C. to 25° C. for 24 h to obtain a product IV; dialyzing and purifying the product IV to obtain a purified product solution, and freeze-drying the purified product solution to obtain purified RGD-PHPMA-b-Poly (MMA-alt-(Rhob-MA)).

The present disclosure further provides a fluorescent polymeric nanomicelle, including the anti-tumor polypeptide Bax-BH3 and the polymer carrier.

The present disclosure further provides a method for preparing the fluorescent polymeric nanomicelle, including the following steps:
1) dissolving a block copolymer RGD-PHPMA-b-Poly (MMA-alt-(Rhob-MA)) in an organic solvent to obtain a block copolymer solution; and
2) adding the block copolymer solution dropwise into an aqueous solution of an anti-tumor polypeptide Bax-BH3 to obtain a fluorescent polymeric nanomicelle.

In some embodiments, in step 1), a concentration of the block copolymer solution may be in a range of 2 mg/mL to 3 mg/mL, and the organic solvent may be THF.

In some embodiments, in step 2), a concentration of the aqueous solution of the anti-tumor polypeptide Bax-BH3 may be in a range of 0.3 mg/mL to 0.7 mg/mL; and performing ultrasonic treatment on the aqueous solution of the polypeptide during the dropwise addition, and each drop of the block copolymer solution may have a volume of 5 μL to 15 μL.

The present disclosure further provides use of the anti-tumor polypeptide Bax-BH3, the anti-tumor drug, the polymer carrier, a polymer carrier prepared by the method for preparing polymer carrier, the fluorescent polymeric nanomicelle, and a fluorescent polymeric nanomicelle prepared by the method for preparing the fluorescent polymeric nanomicelle in preparation of a drug for preventing and/or treating a disease caused by abnormal expression of an anti-apoptotic protein in Bcl-2 family proteins.

In some embodiments, the disease may include a malignant tumor and an autoimmune disease.

Beneficial effects of the present disclosure: the anti-tumor polypeptide Bax-BH3 is a partial sequence of the Bax protein; and cell experiments show that the anti-tumor polypeptide Bax-BH3 is capable of promoting apoptosis. The anti-tumor polypeptide Bax-BH3 includes 20 amino acids, has a small molecular weight; and the polypeptide has desirable biocompatibility and biological activity, which is suitable for tumor treatment. The fluorescent polymeric nanomicelle encapsulates the anti-tumor polypeptide Bax-BH3 by the block copolymer RGD-PHPMA-b-Poly(MMA-alt-(Rhob-MA)), with high encapsulation rate and drug loading, and good release performance.

DETAILED DESCRIPTION OF THE EMBODIMENTS

The present disclosure provides an anti-tumor polypeptide Bax-BH3, having an amino acid sequence set forth in SEQ ID No: 1, specifically as: Asp-Ala-Ser-Thr-Lys-Lys-Leu-Ser-Glu-Cys-Leu-Arg-Arg-Ile-Gly-Asp-Glu-Leu-Asp-Ser. In the present disclosure, a gene encoding the anti-tumor polypeptide has a nucleotide sequence set forth in SEQ ID No: 2, specifically as: ATGGATGCGTCCAC-CAAGAAGCTGAGCGAGTGTCTCCGGCGAATTG-GAGATGAACTG GACAGC. There is no special limitation on the preparation method of the anti-tumor polypeptide Bax-BH3, and conventional preparation methods of the polypeptide in the art can be used.

In a specific implementation process of the present disclosure, a preparation method of the anti-tumor polypeptide Bax-BH3 is preferably as follows: S1) ligating the gene encoding the anti-tumor polypeptide to an expression plasmid to obtain a recombinant vector; and S2) transferring the recombinant vector into cells for expression to obtain the anti-tumor polypeptide Bax-BH3.

In the present disclosure, the gene encoding the anti-tumor polypeptide is ligated to the expression plasmid to obtain the recombinant vector. The gene encoding the anti-tumor polypeptide is preferably artificially synthesized by a biotechnology company; the expression plasmid is preferably a pLVX-mCherry-N1 plasmid; and the gene encoding the anti-tumor polypeptide is preferably ligated between EcoR I and Xho I restriction sites of the pLVX-mCherry-N1 plasmid. PCR amplification is conducted taking the artificially synthesized gene as a template and using sequences set forth in SEQ ID No: 3 and SEQ ID No: 4 as primers, to obtain a DNA fragment with the EcoR I and Xho I restriction sites; the DNA fragment and the pLVX-mCherry-N1 plasmid are subjected to double enzyme digestion with the EcoR I and Xho I, respectively, to obtain a digested DNA fragment and a digested plasmid; and the digested DNA fragment and the digested plasmid are ligated to obtain the recombinant vector. The PCR reaction system and program are preferably shown in Table 1.

TABLE 1

PCR reaction system and program

| Total volume | 50 μL | Reaction program | |
|---|---|---|---|
| Template DNA | 2.0 μL | 95° C. 4 min | |
| 5× Pfu buffer | 5.0 μL | | |
| Upstream | 0.5 μL | 95° C. 30 s | 30 cycles |
| Downstream | 0.5 μL | 60° C. 30 s | |
| dNTP (0.25 mm) | 4.0 μL | 72° C. 1 min | |
| H₂O | 37 μL | 72° C. 10 min | |
| Pfu | 1.0 μL | 4° C. | |

Figure 1:
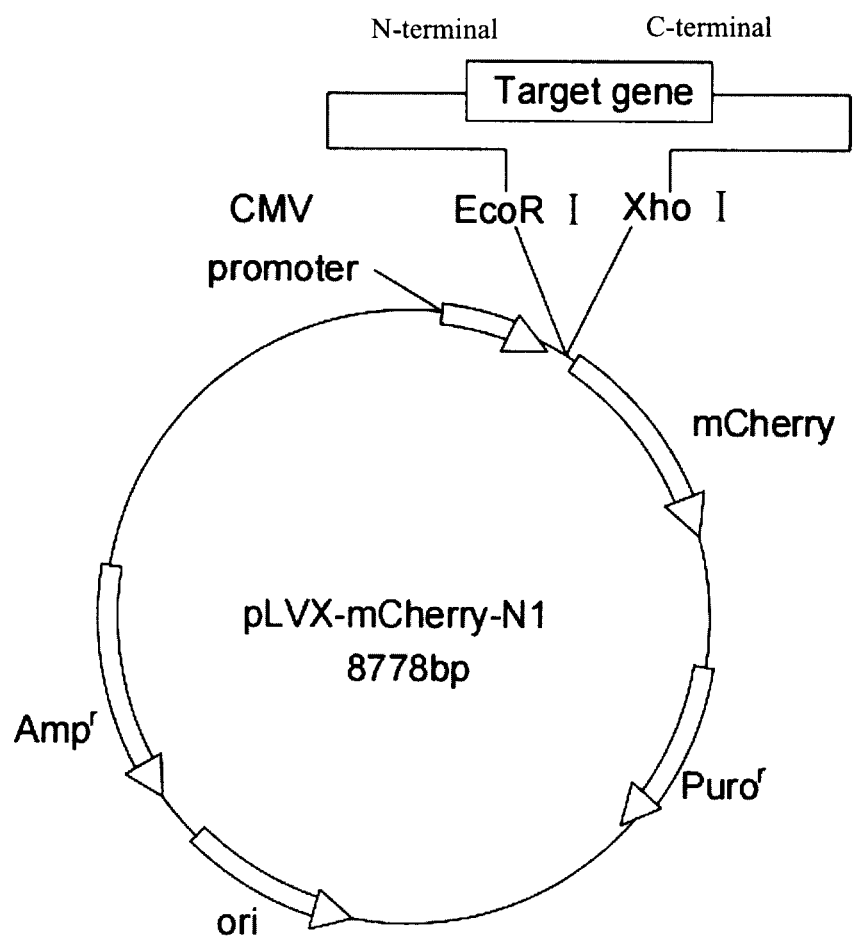
FIG. 1 shows a schematic diagram of a construction model of a recombinant vector.

In the present disclosure, a system of the double enzyme digestion is preferably shown in Table 2. The double enzyme digestion is conducted at preferably 36° C. to 38° C., more preferably 37° C., and a digestion time of the pLVX-mCherry-N1 plasmid is preferably 2.5 h to 3.5 h, more preferably 3 h; and a digestion time of the DNA fragment is preferably 5 h to 7 h, more preferably 6 h. After the double enzyme digestion, ligation is preferably conducted; a ligation system is preferably as shown in Table 3; and the ligation is conducted at preferably 15° C. to 17° C., more preferably 16° C., a time for the ligation is preferably 10 h to 14 h, more preferably 12 h. A structural schematic diagram of the recombinant vector after successful ligation is shown in FIG. 1; a gene encoding the anti-tumor polypeptide Bax-BH3 is inserted between the EcoR I and Xho I restriction sites of pLVX-mCheny-N1, where an N-terminal is ligated to the EcoR I restriction site and a C-terminal is ligated to the Xho I restriction site; the recombinant vector is 8,778 bp in total, including a CVM promoter, mChery, a Puro resistance gene, an on sequence and an Amp resistance gene. The recombinant vector is transformed into stbl3 competent cells for culture and screening after the recombinant vector is obtained; there is no special limitation on the specific method for culture and screening, and conventional culture and conventional screening methods for enzyme digestion, electrophoresis and sequencing in the art can be used.

TABLE 2

Reaction system of double enzyme digestion

| Components | Volume |
|---|---|
| Digested vector or digested DNA | 18 μL |
| Xho I | 2.0 μL |
| EcoR I | 2.0 μL |
| 10× T buffer | 3.0 μL |
| Sterilized deionized water | 5.0 μL |
| Total volume | 30 μL |

TABLE 3

Components and dosages of ligation system

| Components | Volume |
|---|---|
| Linear pLVX-mCherry-N1 vector | 3.0 μL |
| Target gene fragment | 5.0 μL |
| T4 ligase | 1.0 μL |
| 10× reaction buffer | 1.2 μL |
| Sterilized deionized water | 1.8 μL |
| Total volume | 12 μL |

In the present disclosure, after screening to obtain a correct recombinant vector, the recombinant vector is transferred into cells for expression. The cells are preferably HEK-293T cells, there is no special limitation on the method for the transfer, and conventional transfer methods in the art can be used.

In the present disclosure, after being transferred into the recombinant vector, the cells undergo obvious apoptosis; the nucleus is pyknotic, the chromatin is concentrated, the cell becomes round and shrunken while the cell membrane remains intact, where nucleus changes are particularly prominent. It can be seen that the transfer of the recombinant vector containing the gene encoding the anti-tumor polypeptide Bax-BH3 into the HEK-293T cells can promote the occurrence of apoptosis.

The present disclosure further provides a polymer carrier, where the polymer carrier is a block copolymer, named arginyl glycyl aspartic acid-poly(N-(2-hydroxypropyl)methacrylamide)-block polymethacryloyl rhodamine B-polymethyl methacrylate, abbreviated as RGD-PHPMA-b-Poly(MMA-alt-(Rhob-MA)). The block copolymer RGD-PHPMA-b-Poly(MMA-alt-(Rhob-MA)) is obtained by: synthesizing a hydrophobic end Poly(MMA-alt-(Rhob-MA)) by a RAFT reaction using methacryloyl-functionalized rhodamine B and methyl methacrylate (MMA) as hydrophobic end repeating units; polymerizing the Poly(MMA-alt-(Rhob-MA)) with hydroxypropyl methacrylate (HPMA) to synthesize a chain-typed block copolymer PHPMA-b-Poly(MMA-alt-(Rhob-MA)) with one end hydrophilic and one end hydrophobic; and ligating the PHPMA-b-Poly(MMA-alt-(Rhob-MA)) with a targeting peptide RGD by amidation to synthesize the RGD-PHPMAb-Poly(MMA-alt-(Rhob-MA)). A specific preparation method of the polymer carrier is described in the Examples.

The present disclosure further provides an anti-tumor drug, including the anti-tumor polypeptide Bax-BH3 and an auxiliary material. A mass percentage content of the anti-tumor polypeptide Bax-BH3 in the anti-tumor drug is preferably 1% to 99%; there is no special limitation on the types of the auxiliary material, and pharmaceutically acceptable auxiliary materials of the anti-tumor polypeptide Bax-BH3 can be used; and the auxiliary material includes preferably a carrier or an excipient. The carrier is preferably a polymer carrier, in particular a fluorescent block copolymer that is capable of self-assembly into a spherical shape in liquid and has both a hydrophilic group and a hydrophobic group. The drug is suitable for administration by injection.

The present disclosure further provides a fluorescent polymeric nanomicelle, including the anti-tumor polypeptide Bax-BH3 and the polymer carrier. The polymer carrier is preferably a block copolymer, named arginyl glycyl aspartic acid-poly(N-(2-hydroxypropyl)methacrylamide)-block polymethacryloyl rhodamine B-polymethyl methacrylate, abbreviated as RGD-PHPMA-b-Poly(MMA-alt-(Rhob-MA)). The block copolymer RGD-PHPMA-b-Poly(MMA-alt-(Rhob-MA)) is capable of self-assembly into spheres in water to promote preparation of the fluorescent polymeric nanomicelle.

The present disclosure further provides a preparation method of the fluorescent polymeric nanomicelle, including the following steps: 1) dissolving the block copolymer RGD-PHPMA-b-Poly(MMA-alt-(Rhob-MA)) in an organic solvent to obtain a block copolymer solution; 2) dissolving the anti-tumor polypeptide Bax-BH3 in water to obtain a polypeptide solution; and 3) adding the block copolymer solution dropwise into the polypeptide solution to obtain the fluorescent polymeric nanomicelle; where steps 1) and 2) can be conducted in any order.

In the present disclosure, the block copolymer RGD-PHPMA-b-Poly(MMA-alt-(Rhob-MA)) is dissolved in the organic solvent to obtain the block copolymer solution. A concentration of the block copolymer solution is preferably 2 mg/mL to 3 mg/mL, more preferably 2.2 mg/mL to 2.8 mg/mL, and most preferably 2.5 mg/mL; and the organic solvent is preferably THF.

In the present disclosure, the anti-tumor polypeptide Bax-BH3 is dissolved in water to obtain the polypeptide solution. A concentration of the polypeptide solution is preferably 0.3 mg/mL to 0.7 mg/mL, more preferably 0.4 mg/mL to 0.6 mg/mL, and most preferably 0.5 mg/mL. The water is preferably high-purity water.

In the present disclosure, the block copolymer solution is added dropwise into the polypeptide solution to obtain the fluorescent polymeric nanomicelle after obtaining the block copolymer solution and the polypeptide solution. During the dropwise addition, the polypeptide solution is preferably subjected to ultrasonic treatment at 150 W to 250 W, preferably at 200 W; and each drop of the block copolymer solution is preferably 5 µl to 15 µl, more preferably 8 µl to 12 µl, and most preferably 10 µl. A volume ratio of the block copolymer solution to the polypeptide solution is preferably 1:(8-12), more preferably 1:(9-11), and most preferably 1:10; and after the dropwise addition, the ultrasonic treatment is preferably continued for 5 min to 15 min, more preferably for 8 min to 12 min, and most preferably for 10 min. After the ultrasonic treatment, the solvent in the system is preferably removed by rotary evaporation at 45° C. to 55° C., more preferably at 50° C.

The present disclosure further provides use of the anti-tumor polypeptide Bax-BH3, the anti-tumor drug and the fluorescent polymeric nanomicelle in preparation of a drug for preventing and/or treating a disease caused by abnormal expression of an anti-apoptotic protein in Bcl-2 family proteins. The disease includes a malignant tumor and an autoimmune disease; and the malignant tumors include, but are not limited to, lung cancer and malignant hematological tumor-based diseases.

The technical solution provided by the present disclosure will be described in detail below with reference to examples, but they should not be construed as limiting the protection scope of the present disclosure.

Example 1

Synthesis of a Target Gene Fragment

The target gene fragment was synthesized by Comate Bioscience Co., Ltd. in Jilin Province, with a sequence as follows:

(SEQ ID No: 2)
ATGGATGCGTCCACCAAGAAGCTGAGCGAGTGTCTCCGGCGAATTGGAGA

TGAACTGGACAGC.

The primers containing EcoR I and Xho I were designed according to the target gene, the sequences of the primers were as follows: upstream primer sequence was 5'-CCGCTCGAGATGGATGCGTCCACCAAGAAG-3' (SEQ ID No: 3), containing a Xho 1 site (bold); downstream primer sequence was 5'-CCGGAATTCGCTGTCCAGTT-CATCTCC-3' (SEQ ID No: 4), containing an EcoR 1 site (bold); the primers were synthesized by Jilin Comate Bioscience Co., Ltd. PCR amplification was conducted with the synthesized target gene as a template, and reaction conditions were shown in Table 1.

Double Enzyme Digestion of the Target Gene and the pLVX-mCherry-N1 Expression Vector The target gene and the pLVX-mCherry-N1 (purchased from GENEWIZ Biotechnology Co., Ltd., with a product number of DS16071812) were subjected to double enzyme digestion with EcoR I and Xho I, respectively, to obtain DNA fragments with sticky ends; each target gene fragment and linear vector after digestion were detected by 1.0% agarose electrophoresis; the enzyme digestion reaction system was shown in Table 2. The digestion temperature was 37° C., and digestion time of the target gene was 6 h, digestion time of the vector plasmid was 3 h.

Ligation of the Target Gene with the pLVX-mCherry-N1, and Transformation

The target gene and the pLVX-mCherry-N1 vector after double enzyme digestion, a buffer, ddH$_2$O and required enzymes were added into a 0.5 mL sterile EP tube, and the resulting mixture was ligated at 16° C. overnight. The reaction conditions were shown in Table 3. Meanwhile, a control group was treated with only a linear vector, without target DNA fragment. An overnight-ligated product was transformed into stbl3 competent cells. A schematic diagram of a successfully-ligated recombinant vector was shown in FIG. 1.

Screening of the Recombinant Vector

The stbl3 competent cells transformed with the recombinant vector were spread on a petri dish and cultured overnight. A single colony was picked up and added into 3 mL of LB liquid medium containing ampicillin with a final concentration of 100 µg/mL, and incubated overnight at 200 rpm in a constant-temperature shaker at 37° C. The recombinant vector was extracted using an endotoxin-free plasmid extraction kit, and an extracted recombinant vector was digested with aflII enzyme (both 517 bp and 6057 bp of the vector plasmid LVX-mCherry-N1 contained aflII restriction sites), a digested DNA fragment was detected using 1.0% agarose electrophoresis, to observe whether there were target fragments near 5616 bp and 3238 bp; if there was the target fragment, it was determined to be positive. If the result was positive, a sample was sent for sequencing verification.

Transfection of HEK-293T Cells with the Recombinant Vector

The cultured HEK-293T cells (purchased from ATCC) were digested and counted with a hemocytometer, the resulting cells were diluted with a medium containing 10% fetal bovine serum (FBS) by volume, and added to a six-well plate, with $2\times10^5$ cells per well. The six-well plate was incubated in a 5% $CO_2$ incubator at 37° C. until the cells grew to 50% to 70% confluence for transfection.

The experiments were performed in five groups, namely a blank control group (as CTL), a group containing only transfection reagent (as PEI), a group of a control plasmid transfected with the transfection reagent (the control plasmid was purchased from GENEWIZ: 80-322406707_R4) (as PEI/pLVX-C), a group of the recombinant vector transfected with the transfection reagent (as PEI/pLVX-BH3), and a group of adding a Z-VAD-FMK inhibitor (as inhibit/PEU/pLVX-BH$_3$).

During the transfection, a mass-to-volume ratio (m:v) of the plasmid and the transfection reagent was 1:2, and 1 µg of the plasmid was added to each well of the six-well plate, and 2 µl of the transfection reagent was added correspondingly; the plasmid and transfection reagent were diluted with a serum-free medium in advance, shaken well, and allowed to stand at 25° C. for 5 min separately; the transfection reagent was pipetted to the serum-free medium containing the plasmid, flicked to mix well, and allowed to stand at 25° C. for 20 min to obtain a complex. The original medium in the cells was changed to the serum-free medium, the complex was slowly added to the medium, and shaken well to obtain a mixture; the mixture was placed in a 37° C. incubator for 4 h, a serum-free transfection solution in the incubated mixture was removed by suction, and a normal medium was replaced, then the resulting mixture was continued to be cultured for 12 h. Z-VAD-FMK (Selleck) was added to the six-well plate at a concentration of 20 µM 2 h before the transfection, nuclei were colored with a Hoechst 33342 dye, and condition of the cells after transfection was observed under a fluorescence microscope.

Figure 2:
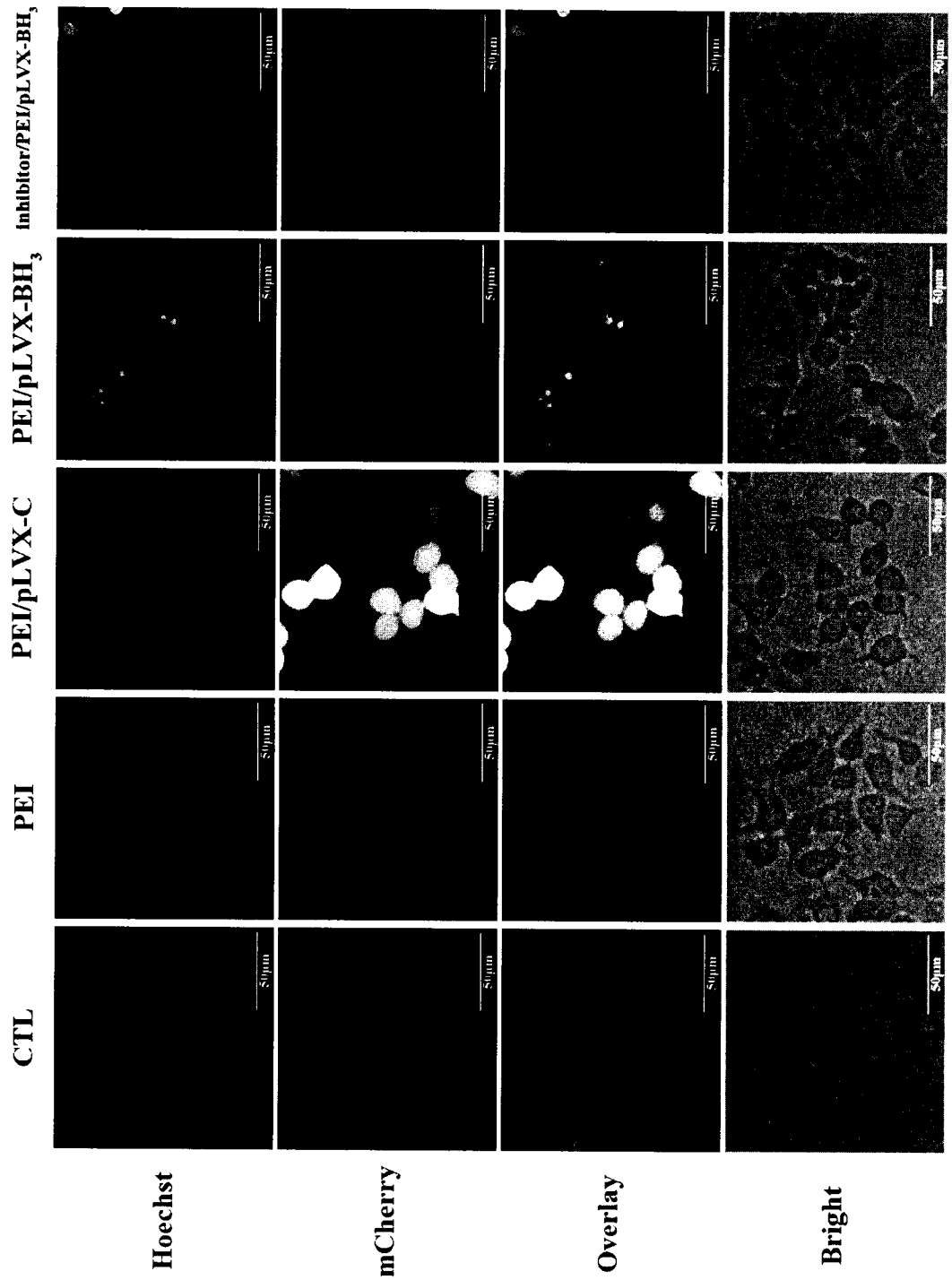
FIG. 2 shows a state of cells after transfection with a recombinant vector under a fluorescence microscope.
Figure 3:
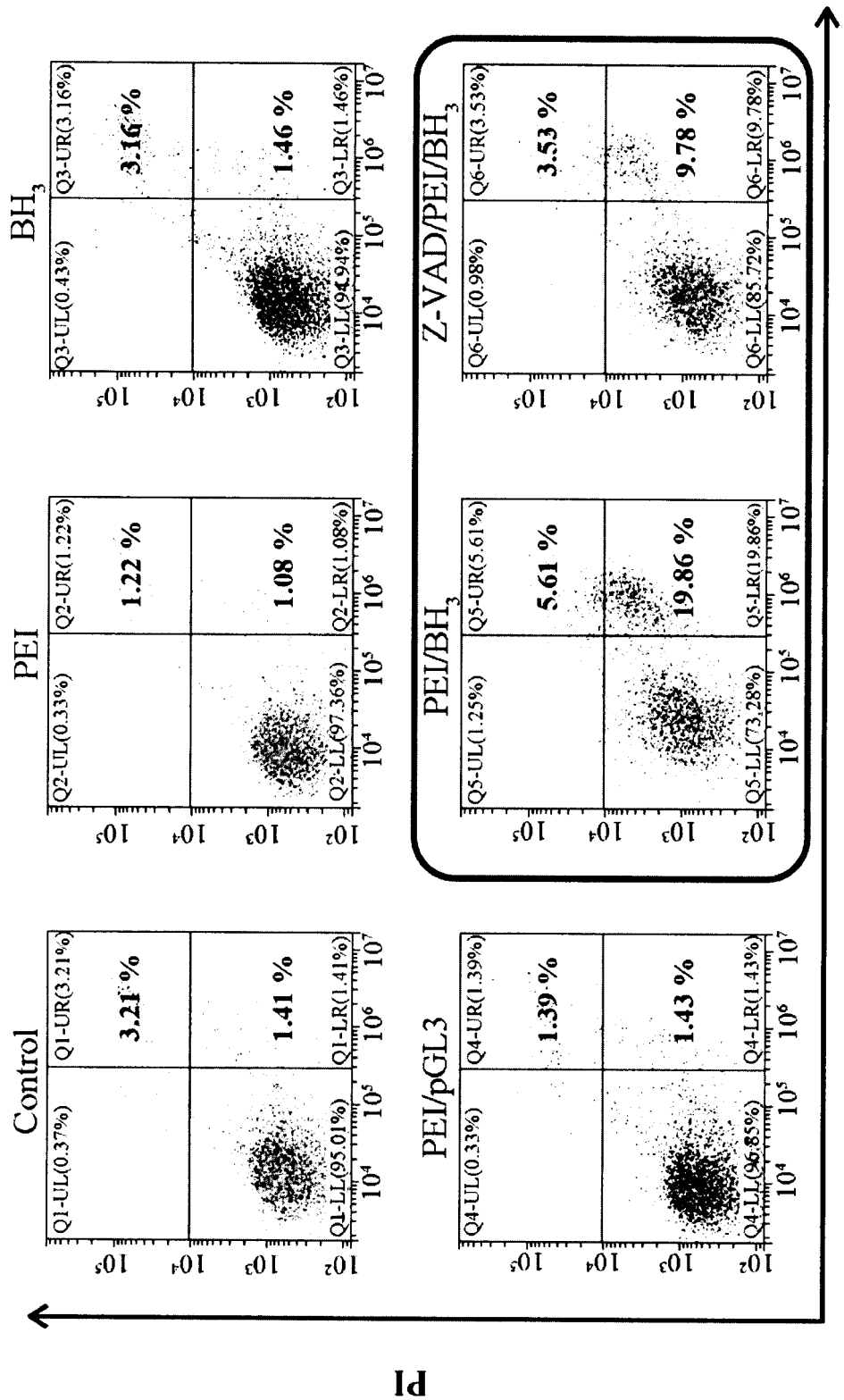
FIG. 3 shows results of apoptosis by Annexin V-FITC flow detection.

The results are shown in FIG. 2. The cells in the blank control group and the group containing only the transfection reagent are in desirable conditions, and do not contain red fluorescence since a fluorescent plasmid is not transferred; while red fluorescence were observed in the other three groups under the microscope due to the transfer of fluorescent plasmids into the cells in the other three groups, indicating that the transfection experiment is successful. In the group transfected with the control plasmid with transfection reagent, it can be observed that the cell state has hardly changed, but after the transfection of the recombinant vector containing the gene encoding the Bax-BH3 polypeptide, the cells undergo obvious apoptosis; the nucleus is pyknotic, the chromatin is concentrated, the cell becomes round and shrunken while the cell membrane remains intact, where nucleus changes are particularly prominent. It can be seen that the addition of the inhibitor can significantly inhibit apoptosis. Therefore, transfection of the recombinant vector containing the gene encoding Bax-BH3 polypeptide into the HEK-293T cells can promote the occurrence of apoptosis.

The transfected cells were further detected using an Annexin V-FITC flow cytometry-based apoptosis assay, specific steps were as follows: the HEK-293T cells were digested with EDTA-free trypsin and collected; the digested cells were washed twice with PBS (centrifugation at 1,000 rpm for 5 min) to collect $1\times10^5$ to $5\times10^5$ cells; the collected $1*10^5$ to $5\times10^5$ cells were resuspended with 400 µL of a Binding Buffer; 2 µL of Annexin V-FITC was added to the suspension and mixed well as mixture I, and 2 µL of Propidium Iodide was added to mixture I and mixed well as mixture II; mixture II was reacted at room temperature in the dark for 10 min; and within 1 h, apoptosis was detected by flow cytometry. The results are shown in Table 2.

TABLE 2

Survival rate of cells transfected with recombinant vector detected by Annexin V-FITC flow cytometry-based apoptosis assay

| Groups | Apoptosis rate (%) |
|---|---|
| CTL | 5.77 ± 1.12 |
| PEI | 3.02 ± 0.71 |
| BH3 | 5.92 ± 1.25 |
| PEI/pGL3 | 4.05 ± 1.11 |
| PEI/BH3 | 27.68 ± 2.12 |
| Z-VAD/PEI/BH3 | 15.07 ± 1.9 |

Figure 4:
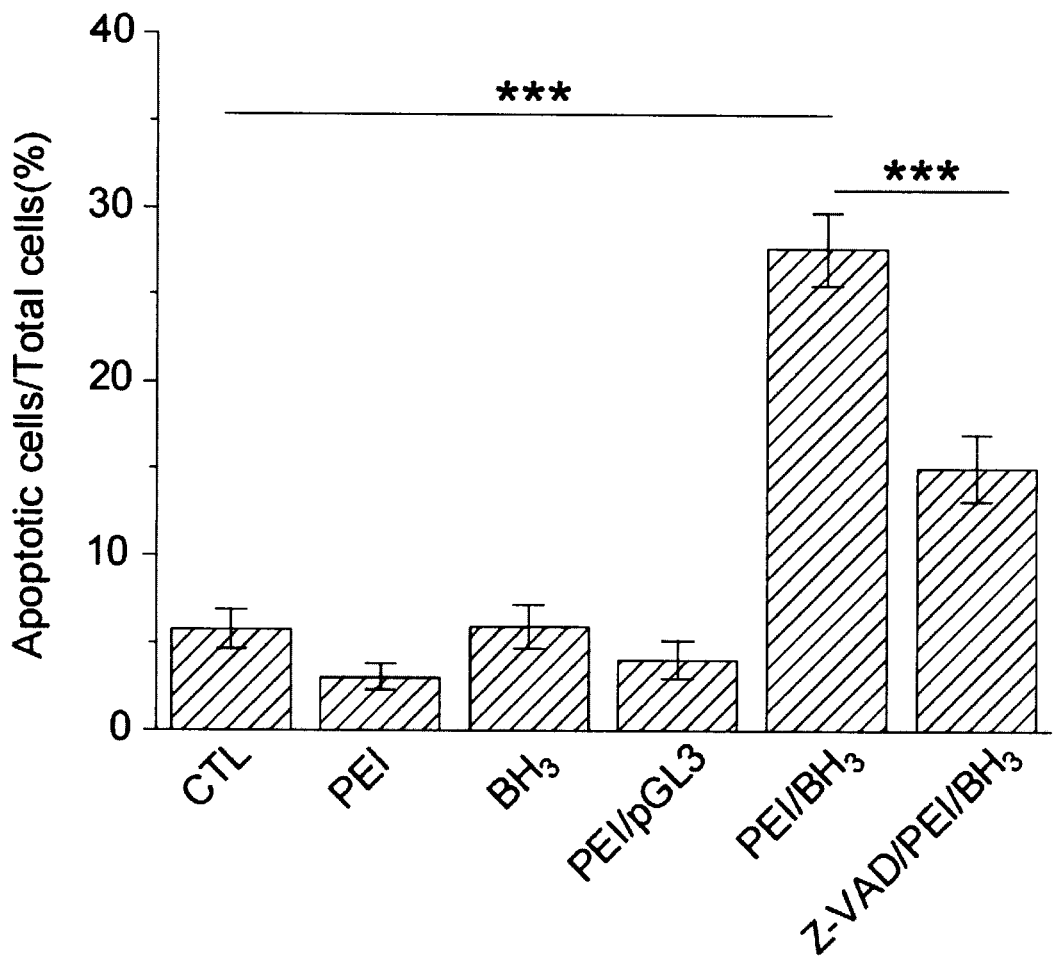
FIG. 4 shows a survival rate of cells transfected with the recombinant vector by Annexin V-FITC flow cytometry-based apoptosis assay; where data is shown as mean t SD (n=3), ***p<0.001.

Since a fluorescence intensity of the control plasmid was stronger after transfection, resulting in great interference to the detection results by flow cytometry-based apoptosis assay, the experiment was conducted using a pGL3-basic vector without red fluorescence as a replacement for the control plasmid group. The results were quantified to obtain a histogram of FIG. 4. As can be seen from the comparison in FIG. 4, the survival rate of cells in the recombinant vector-transfected group is greatly reduced, which is because that after the recombinant vector is transfected into the cells, the Bax-BH3 polypeptide produced by the expression of target gene causes apoptosis, while on this basis, after adding the apoptosis inhibitor Z-VAD-FMK, the cell survival rate is significantly improved. It can be seen that the Bax-BH3 polypeptide expressed by the recombinant vector transfected into the cell has an effect of promoting apoptosis.

Example 2

Figure 5:
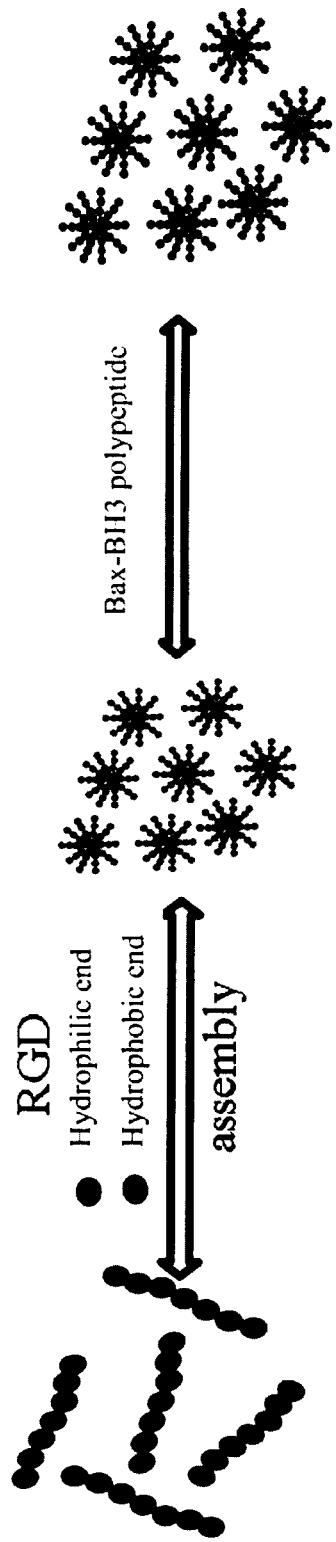
FIG. 5 is a schematic diagram showing an experiment of a Bax-BH3 polypeptide coated with a fluorescent polymeric nanomicelle.

Combination of a Bax-BH3 Polypeptide Coated with a Fluorescent Polymeric Nanomicelle As shown in FIG. 5, a fluorescent block copolymer-based micelle with one end hydrophilic and one end hydrophobic was synthesized using PHPMA as a hydrophilic end, PMMA as a hydrophobic end, rhodamine B as a fluorescent label, and RGD peptide as a targeting peptide (the RGD peptide was purchased from GL Biochem (Shanghai) Co., Ltd.); through a property that the micelle could self-assemble into spheres in water, the Bax-BH3 polypeptide was coated (Bax-BH3 polypeptide was synthesized by GL Biochem (Shanghai) Co., Ltd.).

Figure 6:
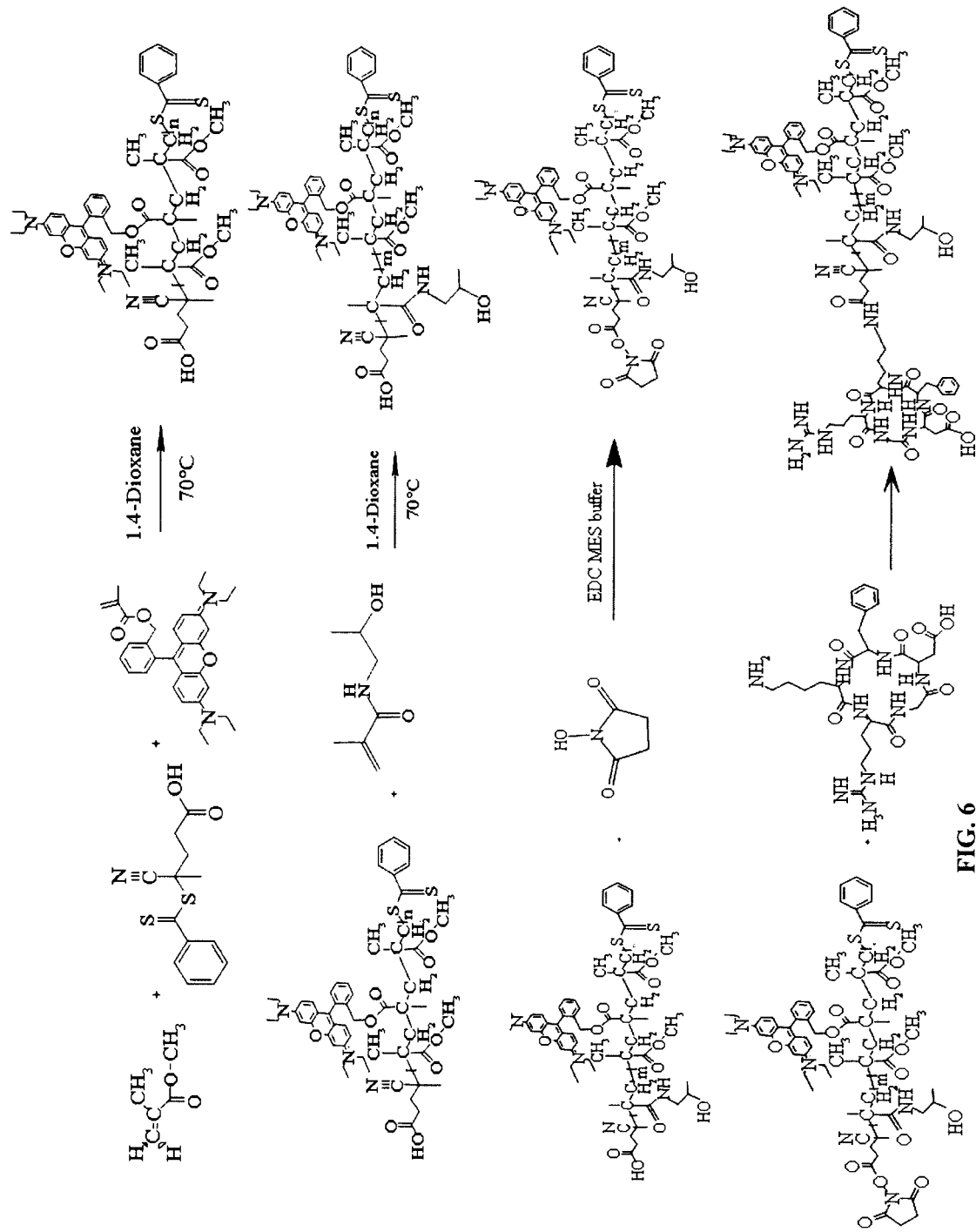
FIG. 6 shows a synthesis strategy of a fluorescent polymer RGD-PHPMA-b-Poly(MMA-alt-(Rhob-MA))

As shown in FIG. 6, a hydrophobic end Poly(MMA-alt-(Rhob-MA)) was synthesized by a RAFT reaction using modified rhodamine B and MMA as hydrophobic end repeating units, and then Poly(MMA-alt-(Rhob-MA)) was polymerized with HPMA to synthesize a chain-typed block copolymer PHPMA-b-Poly(MMA-alt-(Rhob-MA)) with one end hydrophilic and one end hydrophobic; a carboxyl group of the block copolymer was protected by NHS, the RGD-PHPMA-b-Poly(MMA-alt-(Rhob-MA)) was synthesized, and the fluorescent polymeric nanomicelle was prepared by its property of self-assembly into spheres in water.

The specific synthesis process was as follows, in which, raw materials for the reaction were from Beijing Chemical Works and Sigma-Aldrich, America.

The methacryloyl-functionalized rhodamine B was synthesized, including two steps: rhodamine B was reduced to synthesize reduced rhodamine B (Rhob), and the reduced rhodamine B was functional modified with methacryloyl chloride. The specific process was as follows.

1 g of the rhodamine B was dissolved in 37.5 mL of a THF solution, 0.2 g of LiAlH$_4$ was added to the 37.5 mL of the THF solution, the mixed solution was reacted by stirring at room temperature overnight for 12 h under N$_2$ protection. 12.5 mL of water was added dropwise to the reaction solution to quench the reaction, followed by filtration, the filtrate was collected and extracted with dichloromethane, the extract was washed with a saturated sodium chloride solution and dried with 6 g of Na$_2$SO$_4$. 60 mg of elemental sulfur and 100 mg of a reactant dried with Na$_2$SO$_4$ were added in a round-bottomed flask, and reacted at 160° C. for 30 min under N$_2$ protection; the obtained product was cooled to room temperature and mixed with 2.95 mL of absolute ethanol, 0.23 mL of concentrated hydrochloric acid and 5.9 mL of distilled water. The obtained mixture was extracted with 5.9 mL of the dichloromethane, the obtained extract was washed with the saturated sodium chloride solution and dried by the Na$_2$SO$_4$. A crude product I was obtained by vacuum drying the dried product. The crude product 1 was purified by column chromatography, with a developing solvent in a ratio of dichloromethane/methanol of 9:1 to obtain a purified product Rhob.

25 mg of methacryloyl chloride, 50 mg of triethylamine, and 75 mg of the Rhob were reacted in dichloromethane at room temperature overnight. A resulting mixture was washed with distilled water and dried over anhydrous sodium sulfate, followed by vacuum drying to obtain a crude product 2, which was purified by column chromatography. The developing solvent for column chromatography had a ratio of dichloromethane/methanol of 9:1. The methacryloyl-functionalized rhodamine B (Rhob-MA) was obtained after purification.

A block copolymer was synthesized, named arginyl glycyl aspartic acid-poly(N-(2-hydroxypropyl)methacrylamide)-block polymethacryloyl rhodamine B-polymethyl methacrylate, abbreviated as RGD-PHPMA-b-Poly(MMA-alt-(Rhob-MA)). The synthesis included three steps: the synthesis of Poly(MMA-alt-(Rhob-MA)), the synthesis of PHPMA-b-Poly(MMA-alt-(Rhob-MA)), and the synthesis of RGD-PHPMA-b-Poly Synthesis of (MMA-alt-(Rhob-MA)). The specific process was as follows:

Synthesis of Poly(MMA-alt-(Rhob-MA)): 5 mL of MMA, 25 mg of CPADB, 3 mg of AIBN, and 12 mg of Rhob-MA were reacted under N$_2$ protection and using THF as a reaction solvent at 70° C. for 6 h after three times of freeze-thawing and degassing, an obtained product I was precipitated with petroleum ether, and vacuum-dried to obtain a purified product Poly(MMA-alt-(Rhob-MA)).

Synthesis of PHPMA-b-Poly(MMA-alt-(Rhob-MA)): 50 mg of HPMA, 3 mg of the AIBN, and 36 mg of the Poly(MMA-alt-(Rhob-MA)) were reacted under N2 protection and using the THF as a reaction solvent at 70° C. for 12 h after three times of freeze-thawing and degassing, an obtained product II was precipitated with diethyl ether, and vacuum-dried to obtain a purified product PHPMA-b-Poly (MMA-alt-(Rhob-MA)).

Synthesis of RGD-PHPMA-b-Poly(MMA-alt-(Rhob-MA)); 0.5 mg of NHS, 0.8 mg of EDC, and 26 mg of the PHPMA-b-Poly(MMA-alt-(Rhob-MA)) were reacted with a MES buffer as a reaction solvent at room temperature for 24 h. After drying, an obtained product III was filtered with the THF, and a filtrate was collected to obtain a purified product NHS-PHPMA-b-Poly(MMA-alt-(Rhob-MA)); and 26 mg of the NHS-PHPMA-b-Poly(MMA-alt-(Rhob-MA)) and 8 mg of arginyl glycyl-aspartic acid (RGDfK) were reacted with the MES buffer as a reaction solvent at room temperature for 24 h. An obtained product IV was purified by dialysis for 48 h to obtain a purified product solution; and the purified product solution was freeze-dried to obtain purified RGD-PHPMA-b-Poly(MMA-alt-(Rhob-MA)).

Figure 7:
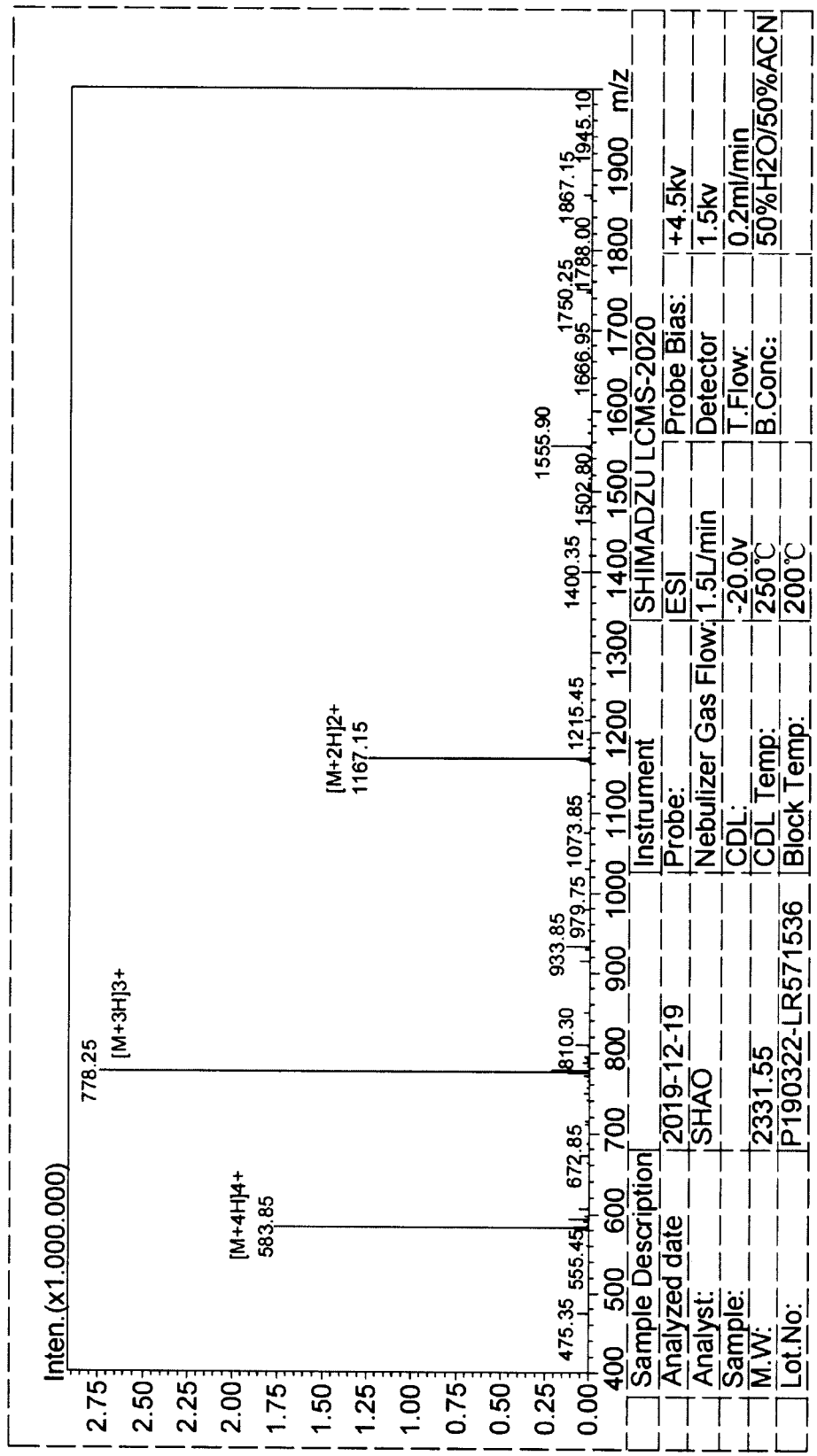
FIG. 7 is an electrospray ionization (ESI) mass spectrum of the Bax-BH3 polypeptide.

The ESI mass spectrum of Bax-BH3 is shown in FIG. 7, and a calculated molecular weight is 2331, which is consistent with the results in FIG. 7.

2.5 mg of a dried block copolymer RGD-PHPMA-b-Poly (MMA-alt-(Rhob-MA)) was dissolved in 1 mL of a THF solvent. 5 mg of the Bax-BH3 polypeptide was dissolved in 10 mL of high-purity water; under ultrasonic conditions, the polymer solution was added dropwise (10 μL/each time) into the Bax-BH3 polypeptide solution; and the ultrasonic treatment was continued for 10 min. The ultrasonic solution was rotary-evaporated at 50° C. until solvent-free, to obtain a drug-loaded nanomicelle RGD-PHPMA-b-Poly(MMA-alt-(Rhob-MA))@BH3.

According to the same method, PHPMA-b-Poly(MMA-alt-(Rhob-MA)@BH3 and an empty vector PHPMA-b-Poly (MMA-alt-(Rhob-MA) were prepared without adding the RGD and without adding the Bax-BH3 polypeptide as controls, respectively.

Figure 8:
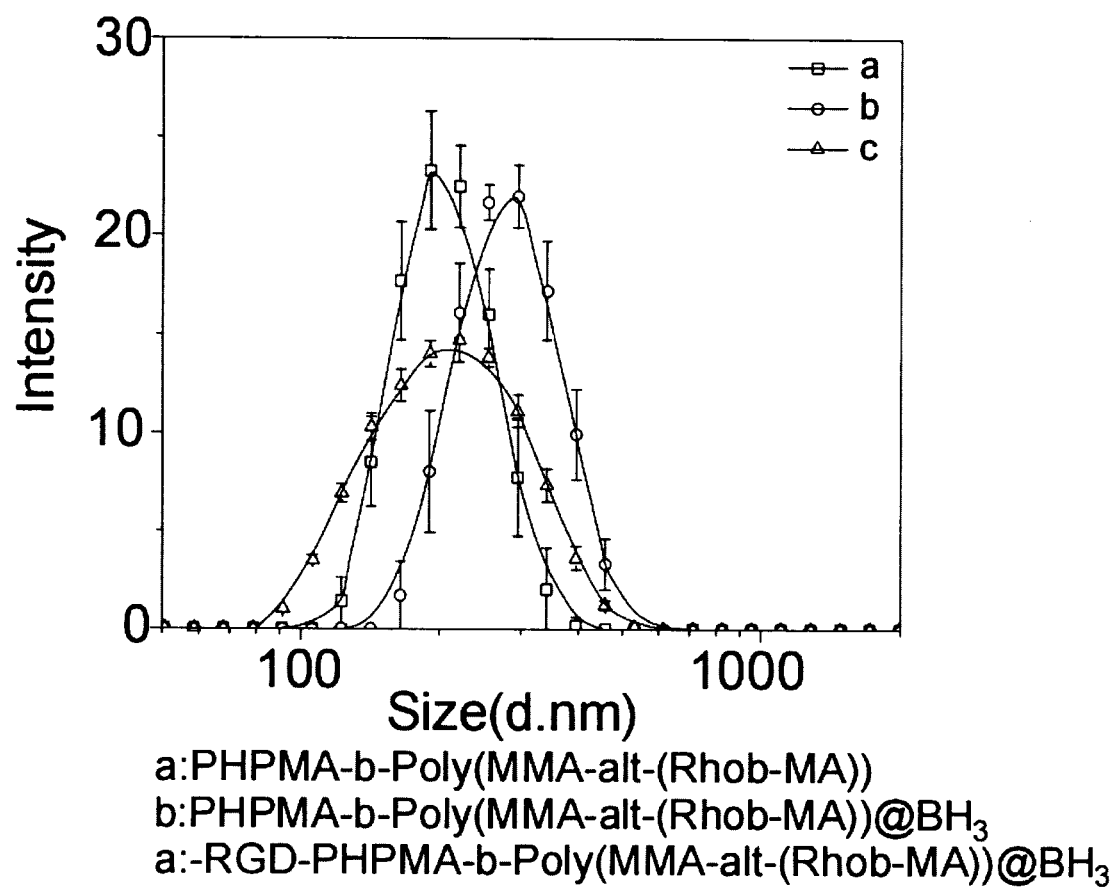
FIG. 8 shows particle size analysis results of three fluorescent polymeric nanomicelles PHPMA-b-Poly(MMA-alt-(Rhob-MA), PHPMA-b-Poly(MMA-alt-(Rhob-MA)@BH3, and RGD-PHPMA-b-Poly(MMA-alt-(Rhob-MA))@BH3.

The three materials were subjected to particle size analysis, and results were shown in FIG. 8. The three fluorescent polymers self-assemble in water to form nanomicelles with good dispersion and uniform particle size. The average particle diameter of the three nanomicelles is in a range of 180 nm to 260 nm, and PDI is less than 0.24. The particle size of the drug-loaded nanomicelle connected with RGD is smaller than that of the non-RGD-connected nanomicelle, and the particle size of the non-drug-loaded nanomicelle is smaller than that of the drug-loaded nanomicelle.

Figure 9:
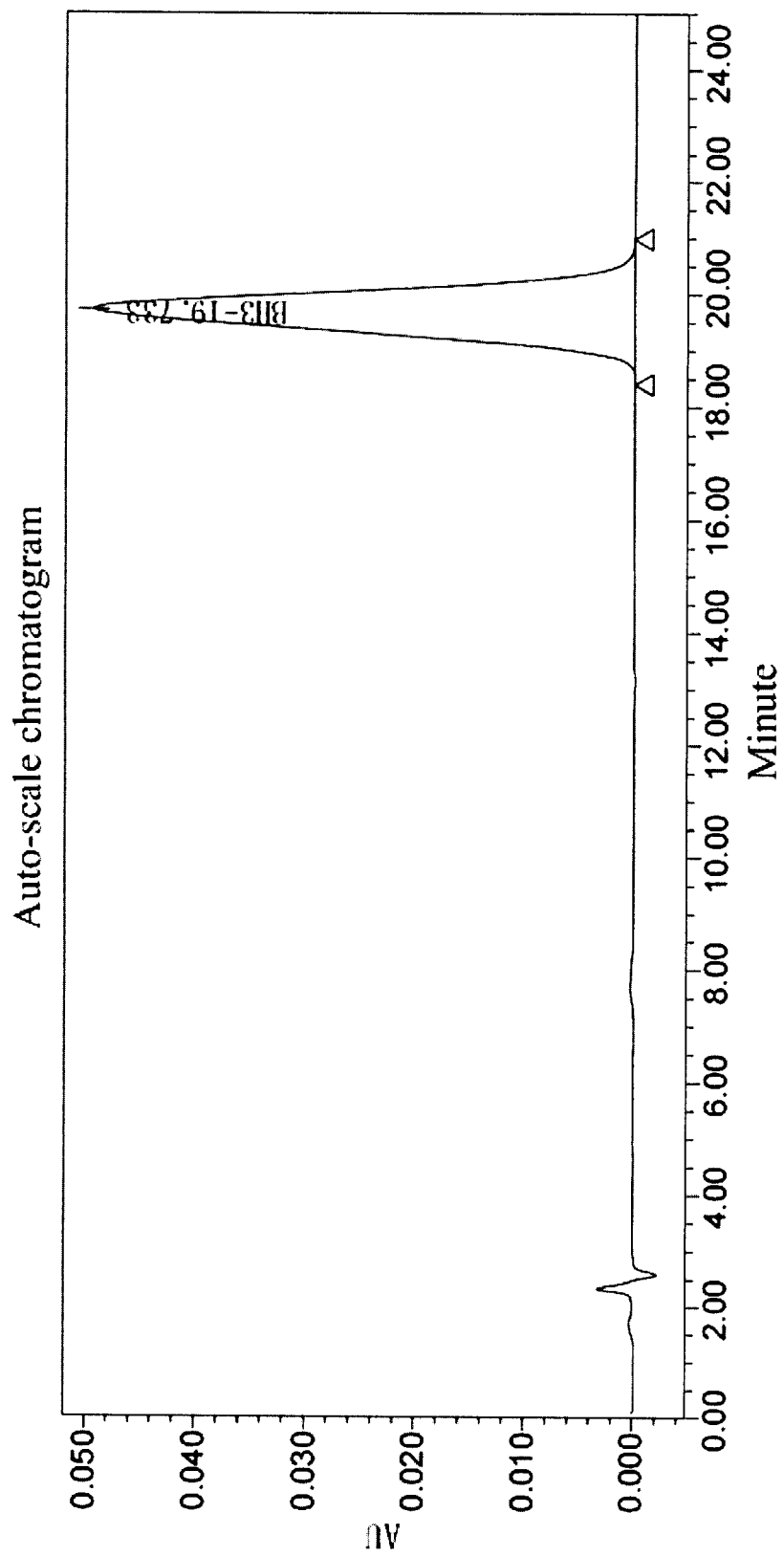
FIG. 9 is an high-performance liquid chromatography (HPLC) chromatogram of a pure Bax-BH3 polypeptide.
Figure 10:
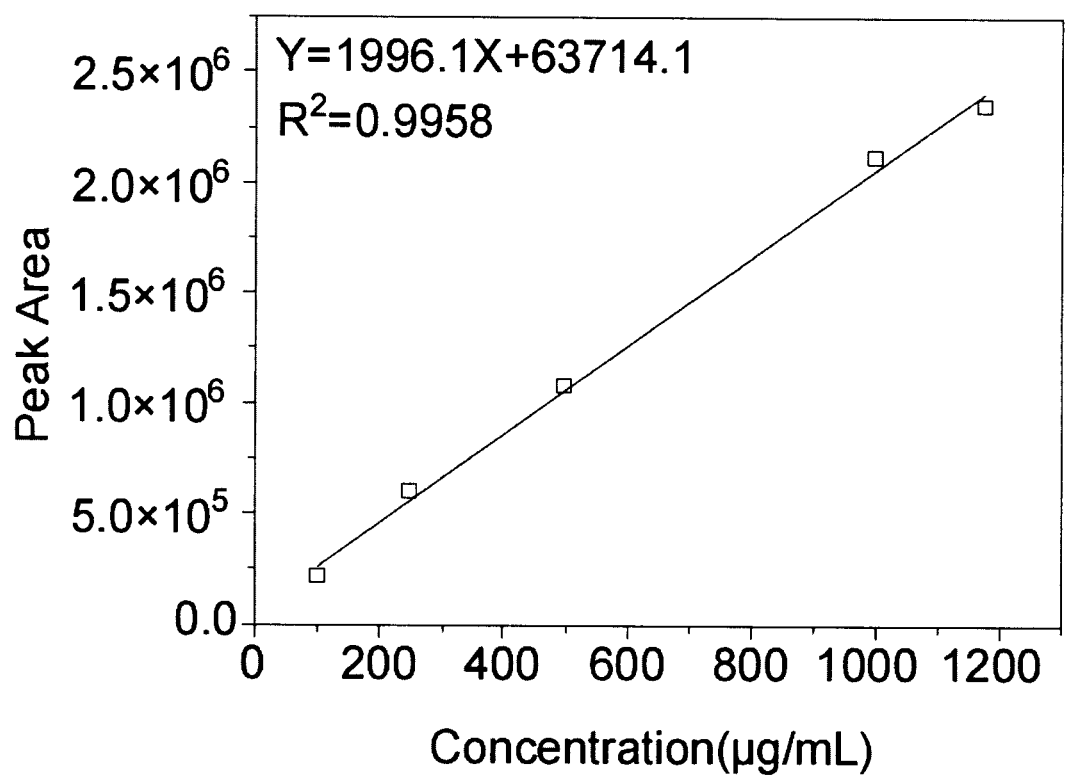
FIG. 10 shows a standard curve of the Bax-BH3 polypeptide.

The drug loading and encapsulation rate of nanomicelle were determined by HPLC under the chromatographic conditions of C18 chromatographic column (5μ 250×4.6 mm), column temperature of 35° C., and water as mobile phase A and acetonitrile as mobile phase B with a flow rate of 1.0 mL/min, detection wavelength of 220 nm, and an injection volume of 10 μL. The HPLC chromatogram of Bax-BH3 polypeptide standard is shown in FIG. 9, with a peak time of 19.733 min and a peak shape of single peak, indicating that the standard is of desirable purity. The Bax-BH3 polypeptide was prepared at 1,175 μg/mL, 1,000 μg/mL, 500 μg/mL, 250 μg/mL, and 100 μg/mL. The HPLC experiment was conducted using the above column conditions, and a standard curve was plotted according to the concentration and peak area. The results are shown in FIG. 10.

Figure 11A:
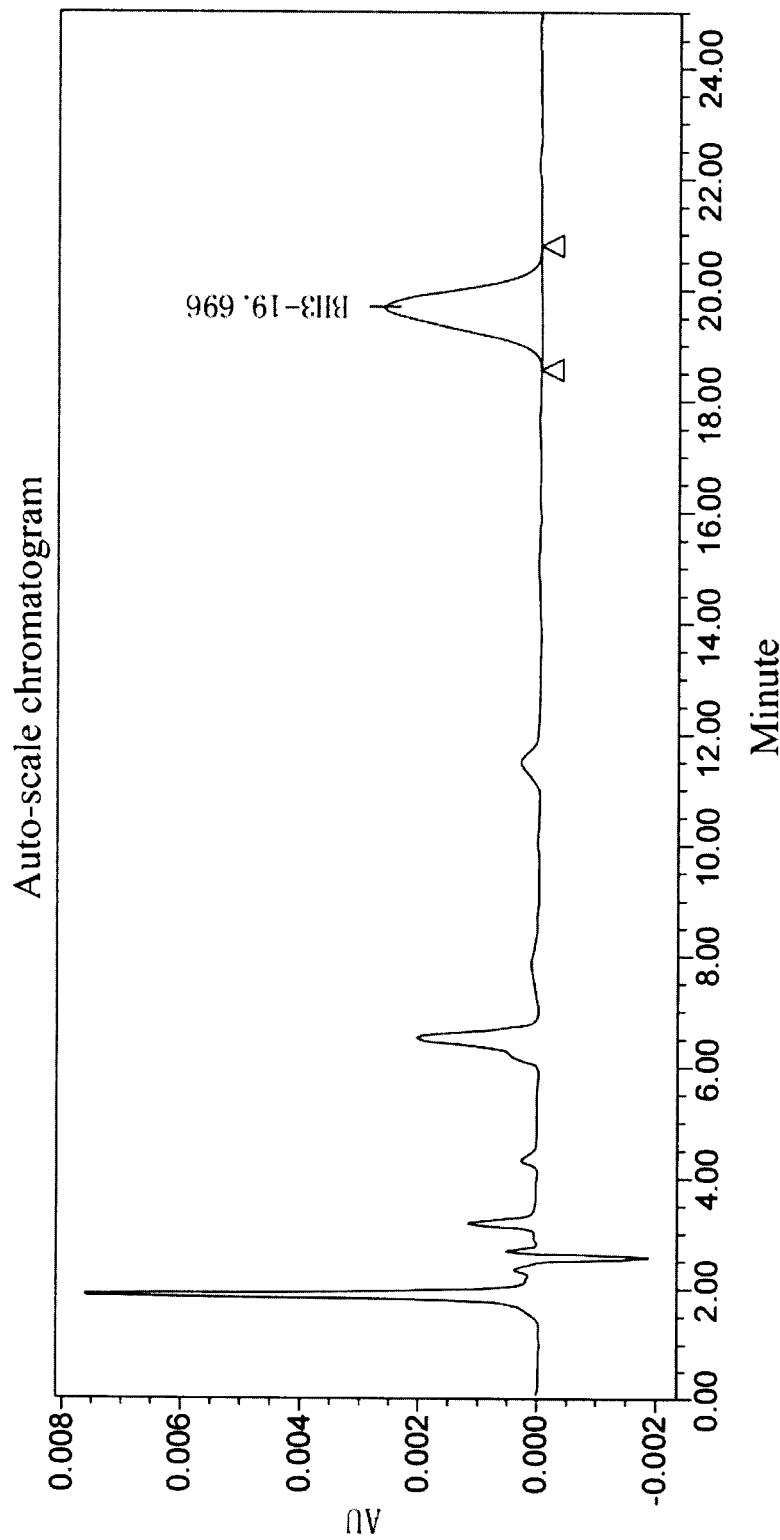
FIG. 11A and FIG. 11B are HPLC chromatograms of the Bax-BH3 polypeptide in two drug-loaded micelles.
Figure 11B:
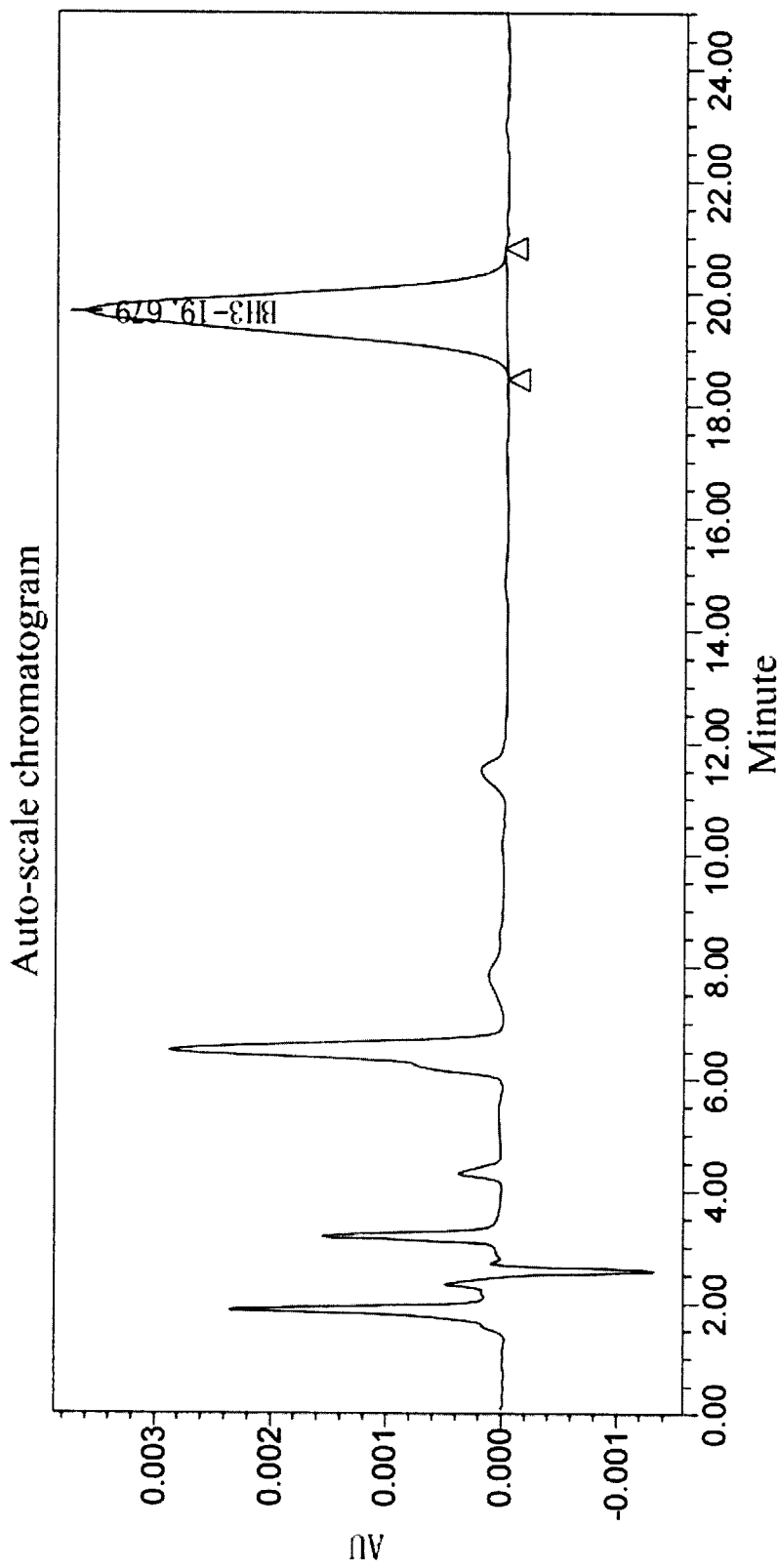

1 mL of the drug-loaded nanomicelle was placed in an EP tube, 200 μL of an acetonitrile solution was added to destroy a polymer micelle structure, and a supernatant was collected by centrifugation; an absorption peak area of a drug released from the sample was determined by HPLC at a wavelength of 220 nm, and drug loading of the drug-loaded micelle was determined according to the standard curve. FIG. 11A and FIG. 11B show HPLC chromatograms of the Bax-BH3 polypeptide in two drug-loaded micelles. The drug-loaded micelles each have desirable encapsulation rate and drug loading; the encapsulation rate and drug loading of PHPMA-b-Poly(MMA-alt-(Rhob-MA))@dBH3 are 11% and 9.10%, respectively; and the encapsulation rate and drug loading of RGD-PHPMA-b-Poly(MMA-alt-(Rhob-MA))@BH3 are 14% and 15.20%, respectively.

Characterization of in vitro release of the nanomicelle. The nanomicelle belongs to a sustained-release drug delivery system, and in vitro release experiments are required to evaluate the preparations. Although there is no correlation between in vitro and in vivo, a preparation technology of the sustained-release drug delivery system is more complicated than that of ordinary preparations. In vitro release may reflect the consistency of product quality between batches, and may also intuitively indicate whether the micelle drug delivery system really has a sustained-release effect.

Figure 12:
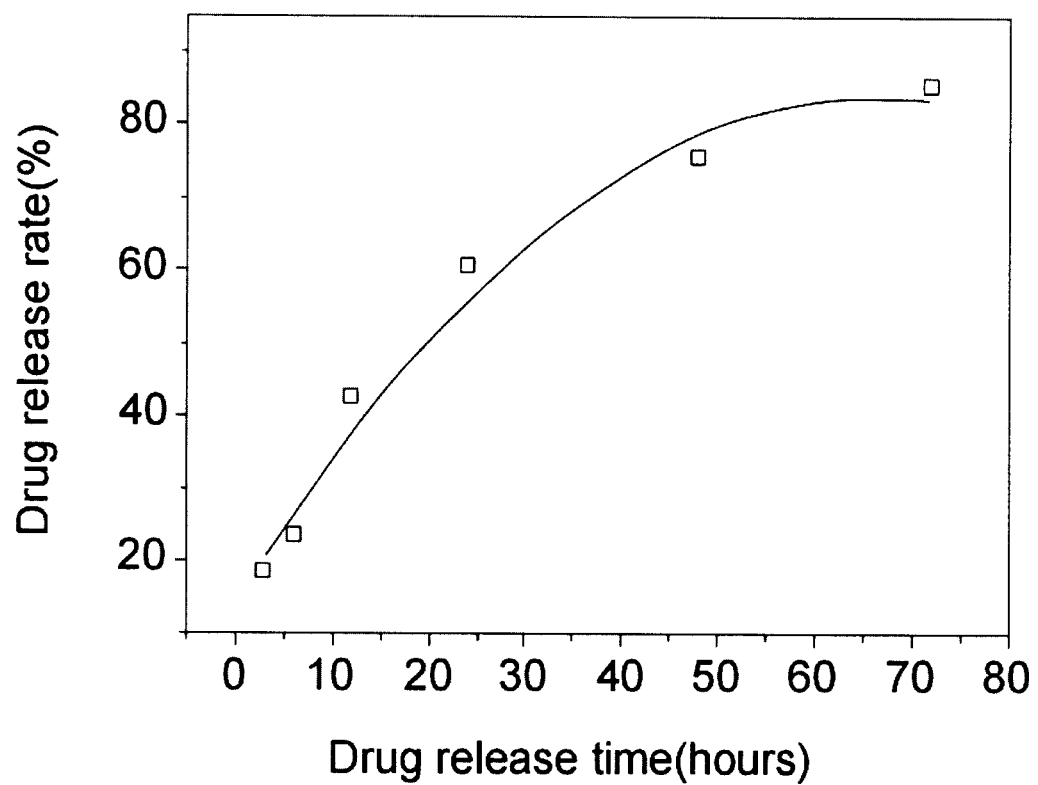
FIG. 12 shows a drug release curve of the PHPMA-b-Poly(MMA-alt-(Rhob-MA))@BH3.

Nanomicelles without targeting peptide RGD was used as an experimental material in subsequent cell experiments, and the targeting peptide had little effect on drug release and experimental results at the cell level. Therefore, PHPMA-b-Poly(MMA-alt-(Rhob-MA)) was selected as a sample for drug release. PBS with pH value of 7.2 was used as a release medium, at 37° C., 10 mL of a PHPMA-b-Poly(MMA-alt-(Rhob-MA))@BH3 solution was added into a prepared dialysis bag (with a molecular weight cut-off of 5,000 D), and the dialysis bag was put into a beaker containing a medium after sealing; samples were sampled at 6 time points of 0 h, 6 h, 12 h, 24 h, 48 h, and 72 h separately, and centrifuged, and absorption peak areas of the 6 samples at a wavelength of 220 nm were detected by HPLC; a release amount of Bax-BH3 polypeptide was calculated by using a standard curve of Bax-BH3 polypeptide as a reference, and an in vitro drug release curve was drawn according to the average value of each group of data. The results are shown in FIG. 12.

Individual polypeptides need to enter cells with the help of nanomicelle. Moreover, the nanomicelle is similar in size to most large proteins (both are nano-scale), so that the nanomicelle is more difficult to be rejected as a foreign matter in the body. As shown in FIG. 12, the nanomicelle PHPMA-b-Poly(MMA-alt-(Rhob-MA)) shows a sustained-release effect to a certain extent, which is beneficial to the better functioning of the BH3 peptide.

Example 3

Anti-Tumor Research of the Polypeptide Bax-BH3

The effect of the PHPMA-b-Poly(MMA-alt-(Rhob-MA)@4BH3 on a proliferation activity of human lung cancer A549 cells was evaluated by MTT assay. Tumor cells in logarithmic growth phase were inoculated in a 96-well plate at a density of $1\times10^5$ cells/well, and incubated in a DMEM medium for 24 h; the DMEM medium was replaced with the PHPMA-b-Poly(MMA-alt-(Rhob-MA)@BH3, followed by incubation for 24 h; 20 μL of an MTT solution (5 mg/mL) was added, the mixed culture was incubation at 37° C. for 4 h, the MTT-containing medium was removed, and 150 μL of DMSO was added to each well. The well plate was shaken for 10 min, and the absorbance value at 520 nm ($OD_{520}$) was measured by an HBS-1096A microplate reader (Nanjing Detie Laboratory Equipment Co., Ltd). The calculation of cell viability was conducted according to the following formula. Cell viability (%)=($OD_{520}$ of experimental group–$OD_{520}$ of blank control group)/($OD_{520}$ of negative control group–$OD_{520}$ of blank control group)×100%. The biocompatibility of PHPMA-b-Poly(MMA-alt-(Rhob-MA) nanomaterial was determined using the same method.

Figure 13:
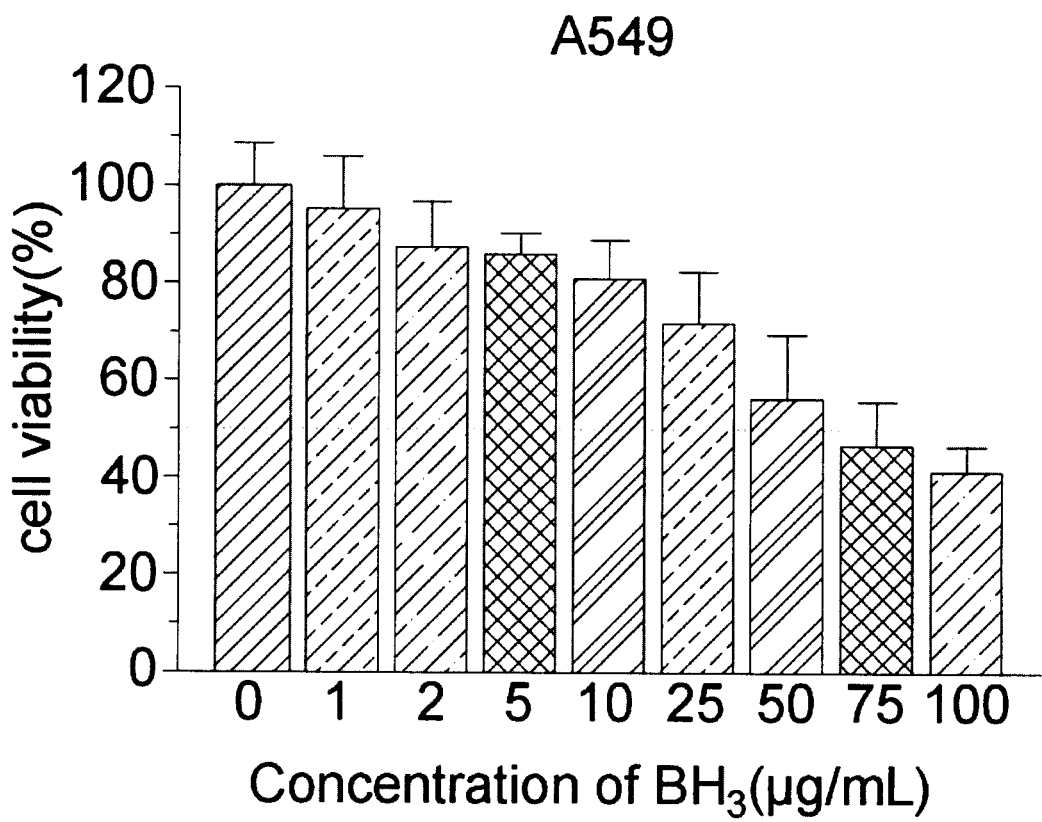
FIG. 13 shows a cytotoxicity experiment results of the PHPMA-b-Poly(MMA-alt-(Rhob-MA)@BH3.
Figure 14:
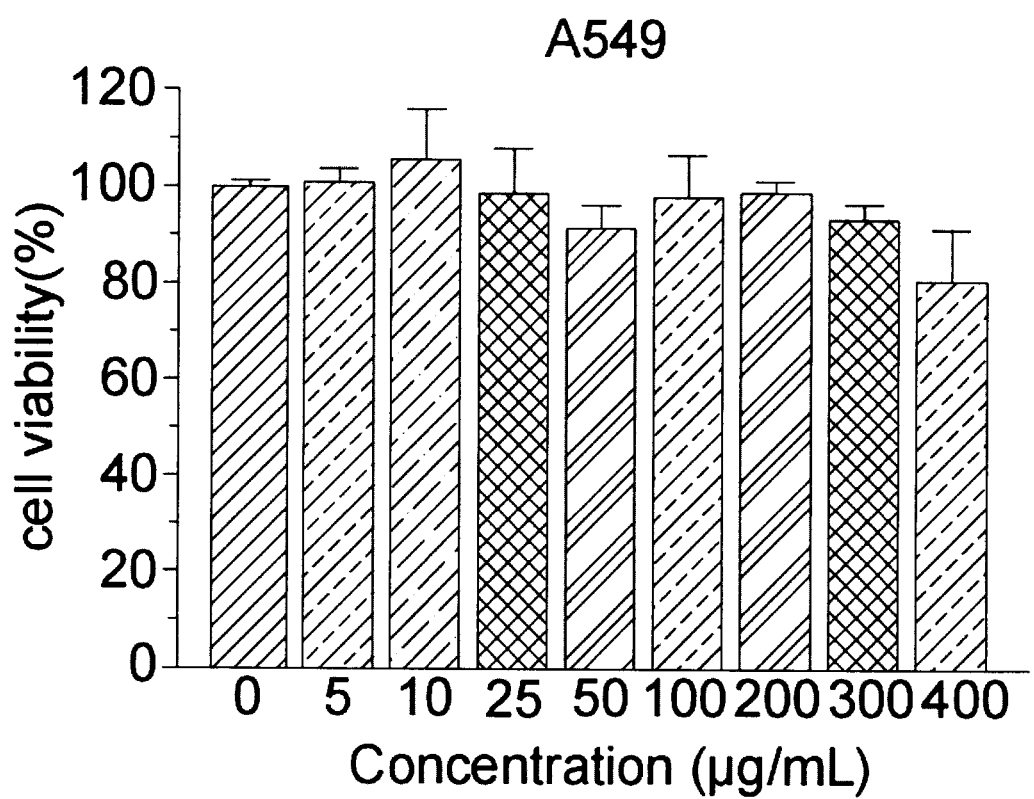
FIG. 14 shows a cytotoxicity experiment results of the PHPMA-b-Poly(MMA-alt-(Rhob-MA) nanomicelle.

The results are shown in FIG. 13 and FIG. 14. After A549 cells are incubated with the PHPMA-b-Poly(MMA-alt-(Rhob-MA) in a concentration of 0 μg/mL to 400 μg/mL for 24 h, the cell viability is above 90%; when the concentration of PHPMA-b-Poly(MMA-alt-(Rhob-MA) is up to 400 μg/mL, the cell viability is over 80%, indicating that even the concentration of PHPMA-b-Poly(MMA-alt-(Rhob-MA) is up to 400 μg/mL, 80% of A549 cells are still alive. However, incubation with PHPMA-b-Poly(MMA-alt-(Rhob-MA)@BH3 may cause severe cytotoxicity to cells, resulting in a significantly decrease in cell viability, indicating that the PHPMA-b-Poly(MMA-alt-(Rhob-MA) nanocarrier has desirable biocompatibility in a concentration of 0 μg/mL to 400 μg/mL, which is a relatively safe drug delivery carrier. The killing effect of PHPMA-b-Poly(MMA-alt-(Rhob-MA)@BH3 on tumor cells mainly results from the Bax-BH3 polypeptide loaded in the nano-drug loading system.

The above descriptions are merely preferred implementations of the present disclosure. It should be noted that, for those skilled in the art, several improvements and modifications will be made without departing from the principle of the present disclosure, but such improvements and modifications should be deemed as falling within the protection scope of the present disclosure.

---

What is claimed is:

1. A fluorescent polymeric nanomicelle, prepared by dissolving a block copolymer RGD-PHPMA-b-Poly(MMA-alt-(Rhob-MA)) in an organic solvent to obtain a block copolymer solution and adding the block copolymer solution dropwise into an aqueous solution of an anti-tumor polypeptide Bax-BH3 having an amino acid sequence set forth in SEQ ID No. 1, to obtain a fluorescent polymeric nanomicelle, the fluorescent polymeric nanomicelle comprising an anti-tumor polypeptide Bax-BH3 and a polymer carrier,
  wherein the anti-tumor polypeptide Bax-BH3 has an amino acid sequence set forth in SEQ ID No. 1, and
  wherein the polymer carrier is a block copolymer, the block copolymer is arginyl glycyl aspartic acid-poly (N-(2-hydroxypropyl)methacrylamide)-block polymethacryloyl rhodamine B-polymethyl methacrylate ("RGD-PHPMA-b-Poly(MMA-alt-(Rhob-MA))").

2. A method for preparing a fluorescent polymeric nanomicelle, comprising the following steps:
  1) dissolving a block copolymer RGD-PHPMA-b-Poly (MMA-alt-(Rhob-MA)) in an organic solvent to obtain a block copolymer solution; and
  2) adding the block copolymer solution dropwise into an aqueous solution of an anti-tumor polypeptide Bax-BH3 having an amino acid sequence set forth in SEQ ID No. 1, to obtain a fluorescent polymeric nanomicelle.

3. The method according to claim 2, wherein in step 1), a concentration of the block copolymer solution is in a range of 2 mg/mL to 3 mg/mL, and the organic solvent is tetrahydrofuran ("THF").

4. The method according to claim 2, wherein in step 2), a concentration of the aqueous solution of the anti-tumor polypeptide Bax-BH3 is in a range of 0.3 mg/mL to 0.7 mg/mL, wherein step 2) further comprises performing ultrasonic treatment on the aqueous solution of the polypeptide during the dropwise addition of the block copolymer solution, and wherein each drop of the block copolymer solution in the dropwise addition of the block copolymer solution has a volume of 5 μL to 15 μL.

5. The method according to claim 2, wherein the block copolymer RGD-PHPMA-b-Poly(MMA-alt-(Rhob-MA)) in step 1) is prepared as follows:
  1) reducing rhodamine B to synthesize reduced rhodamine B, and functional modifying the reduced rhodamine B with methacryloyl chloride to obtain methacryloyl-functionalized rhodamine B ("Rhob-MA");
  2) subjecting methyl methacrylate ("MMA"), 4-cyanopentanoic acid dithiobenzoate ("CPADB"), azobisisobutyronitrile ("AIBN"), and the Rhob-MA to a reaction under $N_2$ protection and using THF as a reaction solvent at 70° C. for 6 h after three times of freeze-thawing and degassing to obtain a product I, precipitating the product I with petroleum ether to obtain a precipitate I, and vacuum-drying the precipitate I to obtain a purified product polymethacryloyl rhodamine B-polymethyl methacrylate ("Poly(MMA-alt-(Rhob-MA))");
  3) subjecting hydroxypropyl methacrylate ("HPMA"), the AIBN, and the Poly(MMA-alt-(Rhob-MA)) to a reaction under $N_2$ protection and by using THF as a reaction solvent at 70° C. for 12 h after three times of freeze-thawing and degassing to obtain a product II, precipitating the product II with diethyl ether to obtain a precipitate II, and vacuum-drying the precipitate II to obtain a purified product PHPMA-b-Poly(MMA-alt-(Rhob-MA));
  4) subjecting N-hydroxy succinimide ("NHS"), 1-ethyl-3-(−3-dimethylaminopropyl) carbodiimide hydrochloride ("EDC"), and the PHPMA-b-Poly(MMA-alt-(Rhob-MA)) to a reaction with a 2-(N-morpholino) ethanesulfonic acid ("MES") buffer as a reaction solvent at 20° C. to 25° C. for 24 h to obtain a product III; drying the product III and filtering with THF, and collecting a filtrate to obtain a purified product NHS-PHPMA-b-Poly(MMA-alt-(Rhob-MA)); and 5) subjecting the NHS-PHPMA-b-Poly(MMA-alt-(Rhob-MA)) and arginyl glycyl aspartic acid ("RGDfK") to a reaction with an MES buffer as a reaction solvent at 20° C. to 25° C. for 24 h to obtain a product IV; dialyzing and purifying the product IV by dialysis to obtain a purified product solution, and freeze-drying the purified product solution to obtain purified RGD-PHPMA-b-Poly(MMA-alt-(Rhob-MA)).

6. A method of treating a patient in need thereof comprising the steps of:
1) selecting a patient having a disease caused by abnormal expression of an anti-apoptotic protein in Bcl-2 family proteins selected from malignant tumors, hematological tumor-based diseases, neurodegenerative diseases, and autoimmune diseases; and 2) administering a therapeutically effective amount of a drug to the patient, the drug comprising a fluorescent polymeric nanomicelle, the fluorescent nanomicelle comprising an anti-tumor polypeptide Bax-BH3 and a polymer carrier prepared in accordance with the method of claim 2,
wherein the anti-tumor polypeptide Bax-BH3 has an amino acid sequence set forth in SEQ ID No. 1, and
wherein the polymer carrier is a block copolymer, the block copolymer is RGD-PHPMA-b-Poly(MMA-alt-(Rhob-MA)).

7. The method according to claim 6, wherein the disease comprises one or more of a malignant tumor and an autoimmune disease.

\* \* \* \* \*